United States Patent
Usuda

(10) Patent No.: US 11,957,299 B2
(45) Date of Patent: Apr. 16, 2024

(54) ENDOSCOPE IMAGE PROCESSING APPARATUS, ENDOSCOPE IMAGE PROCESSING METHOD, AND PROGRAM

(71) Applicant: FUJIFILM Corporation, Tokyo (JP)

(72) Inventor: Toshihiro Usuda, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 749 days.

(21) Appl. No.: 17/080,847

(22) Filed: Oct. 27, 2020

(65) Prior Publication Data

US 2021/0042926 A1 Feb. 11, 2021

Related U.S. Application Data

(63) Continuation of application No. PCT/JP2019/014917, filed on Apr. 4, 2019.

(30) Foreign Application Priority Data

May 15, 2018 (JP) .................................. 2018-093722

(51) Int. Cl.
 *G06F 3/0482* (2013.01)
 *A61B 1/00* (2006.01)
 (Continued)

(52) U.S. Cl.
 CPC .... *A61B 1/000094* (2022.02); *A61B 1/00006* (2013.01); *A61B 1/0005* (2013.01);
 (Continued)

(58) Field of Classification Search
 CPC .......... A61B 1/00006; A61B 1/000094; A61B 1/0005; A61B 1/0638; A61B 1/0684;
 (Continued)

(56) References Cited

U.S. PATENT DOCUMENTS

2006/0025692 A1* 2/2006 Ishihara ............. A61B 1/00096
  600/478
2007/0195165 A1* 8/2007 Hirakawa ............ A61B 1/0005
  348/75

(Continued)

FOREIGN PATENT DOCUMENTS

JP 2009297365 12/2009
JP 2017191461 10/2017

(Continued)

OTHER PUBLICATIONS

Yu Cao, "Computer-Aided Detection of Diagnostic and Therapeutic Operations in Colonoscopy Videos, "Oct. 29, 2006, IEEE Transactions On Biomedical Engineering, vol. 54, No. 7, Jul. 2007, pp. 1268-1274.*

(Continued)

*Primary Examiner* — Omar S Ismail
(74) *Attorney, Agent, or Firm* — JCIPRNET

(57) ABSTRACT

An endoscope image processing apparatus includes: an image acquisition unit that acquires endoscopic images; a detection unit that detects lesion images representing lesions in the endoscopic images acquired by the image acquisition unit; a clustering unit that groups the endoscopic images on the basis of a degree of correlation between the lesion images and generates, for each lesion, a group formed of corresponding ones of the endoscopic images; a representative image selection unit that selects, for each group, a representative image from among the endoscopic images in the group; a saving unit that saves, for each group, the representative image and the endoscopic images that form the group to which the representative image belongs, in association with each other; and a display unit that displays a list of the representative images saved in the saving unit.

20 Claims, 12 Drawing Sheets

(51) Int. Cl.
*G06F 18/23* (2023.01)
*G06T 7/00* (2017.01)
*G06V 20/69* (2022.01)

(52) U.S. Cl.
CPC ............ *G06F 3/0482* (2013.01); *G06F 18/23* (2023.01); *G06T 7/0014* (2013.01); *G06V 20/69* (2022.01); *G06T 2200/24* (2013.01); *G06T 2207/10068* (2013.01); *G06T 2207/30096* (2013.01); *G06V 2201/03* (2022.01)

(58) Field of Classification Search
CPC ....... G02B 23/24; G06F 18/23; G06F 3/0482; G06T 2200/24; G06T 2207/10068; G06T 2207/30096; G06T 7/0014; G06V 20/69; G06V 2201/03; G06V 2201/031
See application file for complete search history.

(56) References Cited

U.S. PATENT DOCUMENTS

| | | | |
|---|---|---|---|
| 2008/0247061 A1* | 10/2008 | Simkulet | G02B 13/06 359/857 |
| 2009/0040235 A1* | 2/2009 | Matsuda | A61B 1/00045 382/128 |
| 2009/0309961 A1 | 12/2009 | Miyashita | |
| 2010/0030021 A1* | 2/2010 | Minai | A61B 5/073 600/109 |
| 2012/0002879 A1* | 1/2012 | Kanda | G06T 7/11 382/195 |
| 2012/0114203 A1* | 5/2012 | Hirota | A61B 1/041 382/128 |
| 2013/0053646 A1* | 2/2013 | Yamamoto | A61B 1/043 600/180 |
| 2013/0152020 A1* | 6/2013 | Nishiyama | G16H 30/20 715/835 |
| 2013/0265401 A1* | 10/2013 | Igarashi | A61B 1/0655 348/68 |
| 2015/0219552 A1* | 8/2015 | Kanamori | G02B 21/365 356/369 |
| 2017/0300664 A1 | 10/2017 | Matsuki | |
| 2018/0047165 A1* | 2/2018 | Sato | G06T 7/74 |
| 2018/0070798 A1* | 3/2018 | Kamiyama | G06T 7/75 |
| 2018/0114319 A1* | 4/2018 | Kono | A61B 1/018 |
| 2019/0089895 A1* | 3/2019 | Kono | A61B 1/04 |
| 2020/0237452 A1* | 7/2020 | Wolf | G06F 3/048 |
| 2020/0273581 A1* | 8/2020 | Wolf | G16H 40/63 |

FOREIGN PATENT DOCUMENTS

| | | |
|---|---|---|
| WO | 2006123455 | 11/2006 |
| WO | 2012132840 | 10/2012 |

OTHER PUBLICATIONS

Konstantin Pogorelov et al. ,"Efficient disease detection in gastro-intestinal videos—global features versus neural networks," Jul. 19, 2017, Multimed Tools Appl 76,2017, pp. 22500-22519.*
Bianca Regeling, "Hyperspectral Imaging Using Flexible Endoscopy for Laryngeal Cancer Detection," Aug. 13, 2016,Sensors 2016,pp. 1-12.*
"International Search Report (Form PCT/ISA/210) "of PCT/JP2019/ 014917, dated Jul. 9, 2019, with English translation thereof, pp. 1-5.
"Written Opinion of the International Searching Authority (Form PCT/ISA/237)" of PCT/JP2019/014917, dated Jul. 9, 2019, with English translation thereof, pp. 1-9.

* cited by examiner

FIG. 6

ENDOSCOPE IMAGE PROCESSING APPARATUS, ENDOSCOPE IMAGE PROCESSING METHOD, AND PROGRAM

CROSS-REFERENCE TO RELATED APPLICATIONS

This application is a Continuation of PCT International Application No. PCT/JP2019/014917 filed on Apr. 4, 2019, which claims priority under 35 U.S.C. § 119(a) to Japanese Patent Application No. 2018-093722 filed on May 15, 2018. Each of the above application(s) is hereby expressly incorporated by reference, in its entirety, into the present application.

BACKGROUND OF THE INVENTION

1. Field of the Invention

The present invention relates to an endoscope image processing apparatus, an endoscope image processing method, and a program.

2. Description of the Related Art

An operator (doctor) needs to prepare a diagnosis report after performing an endoscopic examination. To prepare a diagnosis report, operations of, for example, checking endoscopic images captured during the endoscopic examination and diagnosing a found lesion need to be performed.

During an endoscopic examination, a large number of endoscopic images are acquired regardless of the presence of lesions. When the operator checks all captured endoscopic images and adds, for example, the results of diagnosis to the respective images, the operator's workload becomes heavy.

In an endoscopic examination, a large number of endoscopic images of the same region of interest may be captured from different viewpoints under different image capture conditions. These large number of endoscopic images need to be efficiently managed.

A technique for assisting a user in managing a large number of endoscopic images captured during an endoscopic examination has been proposed to date.

For example, WO2012/132840A describes a technique for adding supplemental information with a simple operation. Specifically, in the technique described in WO2012/132840A, a minified image (for example, 105a or 105b) of an endoscopic image is selected and is dragged and dropped onto an icon in a label box display region 108 to thereby add a lesion label to the desired endoscopic image. For example, in a case of an endoscopic image related to the stomach, examples of the lesion label include an ulcer label, a sore label, a bleeding label, and a cancer label.

SUMMARY OF THE INVENTION

In an endoscopic examination, a large number of endoscopic images are captured for each lesion, and therefore, the large number of endoscopic images may be grouped and a group may be generated for each lesion to thereby provide efficient operations to the user.

When all acquired endoscopic images are displayed on a display unit, the number of displayed endoscopic images becomes excessively large, and the user (operator or doctor) needs to check every endoscopic image, which may increase the user's workload.

The present invention has been made in view of the above-described circumstances, and an object thereof is to provide an endoscope image processing apparatus, an endoscope image processing method, and a program that can provide efficient operations.

An endoscope image processing apparatus, which is an aspect of the present invention for achieving the above-described object, includes: an image acquisition unit that acquires endoscopic images; a detection unit that detects lesion images representing lesions in the endoscopic images acquired by the image acquisition unit; a clustering unit that groups the endoscopic images on the basis of a degree of correlation between the lesion images and generates, for each lesion, a group formed of corresponding ones of the endoscopic images; a representative image selection unit that selects, for each group, a representative image from among the endoscopic images in the group; a saving unit that saves, for each group, the representative image and the endoscopic images that form the group to which the representative image belongs, in association with each other; and a display unit that displays a list of the representative images saved in the saving unit.

According to this aspect, a group formed of endoscopic images is generated for each lesion, a representative image of the generated group is selected, and the representative image and the endoscopic images that form the group to which the representative image belongs are saved in association with each other. Accordingly, this aspect can provide efficient operations to the user. For example, with this aspect, the user can efficiently perform an operation of preparing a report after an endoscopic examination.

Preferably, the endoscope image processing apparatus further includes: an operation input unit that accepts an operation for a representative image among the representative images displayed on the display unit; and an operation control unit that uniformly performs the operation accepted by the operation input unit for all the endoscopic images in the group to which the representative image belongs.

According to this aspect, an operation performed for the representative image is uniformly performed for all the endoscopic images in the group to which the representative image belongs, and therefore, efficient operations can be provided to the user.

Preferably, the operation input unit accepts input of first accessory information to be added to the representative image, and the operation control unit adds the first supplementary information to all the endoscopic images in the group to which the representative image belongs.

According to this aspect, the first supplementary information added to the representative image is added to all the endoscopic images in the group to which the representative image belongs, and therefore, efficient operations can be provided to the user.

Preferably, the operation input unit accepts a change command for changing a group formation of the group, and the operation control unit carries out the change command for all the endoscopic images in the group to which the representative image belongs.

According to this aspect, the change command for changing the group formation carried out for the representative image is carried out for all the endoscopic images in the group to which the representative image belongs, and therefore, efficient operations can be provided to the user.

Preferably, the endoscope image processing apparatus further includes a feature value extraction unit that extracts image feature values of the lesion images detected by the detection unit, and the clustering unit calculates the degree of correlation on the basis the image feature values and generates the group on the basis of the degree of correlation.

According to this aspect, the degree of correlation is calculated on the basis of the image feature values of the lesion images, and the group is generated on the basis of the degree of correlation, and therefore, groups that are accurately formed can be generated.

Preferably, the image acquisition unit acquires the endoscopic images having second supplementary information that is information about capturing of the endoscopic images, and the clustering unit calculates the degree of correlation by using the second supplementary information.

According to this aspect, the second supplementary information that is information about capturing of the endoscopic images is used, and therefore, the degree of correlation can be calculated accurately and efficiently.

Preferably, the representative image selection unit selects, as the representative image, an endoscopic image captured earliest, an endoscopic image captured with white light, an endoscopic image that is blurred to a smallest degree, an endoscopic image in which the lesion is present closest to a center, or an endoscopic image captured without enlargement from among the endoscopic images in the group.

According to this aspect, an endoscopic image that is blurred to the smallest degree, an endoscopic image in which the lesion is present closest to the center, or an endoscopic image captured without enlargement is selected from among the endoscopic images in the group as the representative image, and therefore, an appropriate representative image is selected.

Preferably, the endoscope image processing apparatus further includes a representative image change part that accepts a change command for changing the representative image, and the representative image selection unit changes the representative image to a different endoscopic image among the endoscopic images on the basis of the change command.

According to this aspect, the representative image can be changed, and an appropriate representative image can be displayed on the display unit.

Preferably, the endoscope image processing apparatus further includes a display form selection part that accepts a selection command for selecting a display form of list display by the display unit, and the display unit performs the list display on the basis of a result of selection in the display form selection part.

According to this aspect, the display form of list display can be changed, and therefore, appropriate list display can be provided to the user, and efficient operations can be provided to the user.

Preferably, the image acquisition unit acquires the endoscopic images from an endoscope in real time.

Preferably, the image acquisition unit acquires the endoscopic images already captured and saved during an endoscopic examination.

An endoscope image processing method, which is another aspect of the present invention, includes: an image acquisition step of acquiring endoscopic images; a detection step of detecting lesion images representing lesions in the endoscopic images acquired in the image acquisition step; a clustering step of grouping the endoscopic images on the basis of a degree of correlation between the lesion images and generating, for each lesion, a group formed of corresponding ones of the endoscopic images; a representative image selection step of selecting, for each group, a representative image from among the endoscopic images in the group; a saving step of saving, for each group, the representative image and the group to which the representative image belongs, in association with each other; and a display step of displaying a list of the representative images saved in the saving step.

A program, which is yet another aspect of the present invention, causes a computer to perform an endoscope image processing method including: an image acquisition step of acquiring endoscopic images; a detection step of detecting lesion images representing lesions in the endoscopic images acquired in the image acquisition step; a clustering step of grouping the endoscopic images on the basis of a degree of correlation between the lesion images and generating, for each lesion, a group formed of corresponding ones of the endoscopic images; a representative image selection step of selecting, for each group, a representative image from among the endoscopic images in the group; a saving step of saving, for each group, the representative image and the group to which the representative image belongs, in association with each other; and a display step of displaying a list of the representative images saved in the saving step.

According to the present invention, a group formed of endoscopic images is generated for each lesion, a representative image of the generated group is selected, and the representative image and the endoscopic images that form the group to which the representative image belongs are saved in association with each other, and therefore, efficient operations can be provided to the user.

BRIEF DESCRIPTION OF THE DRAWINGS

FIG. 6 is a diagram for describing example list display of representative images;

DESCRIPTION OF THE PREFERRED EMBODIMENTS

Hereinafter, preferred embodiments of an endoscope image processing apparatus, an endoscope image processing method, and a program according to the present invention will be described with reference to the attached drawings.

Figure 1:
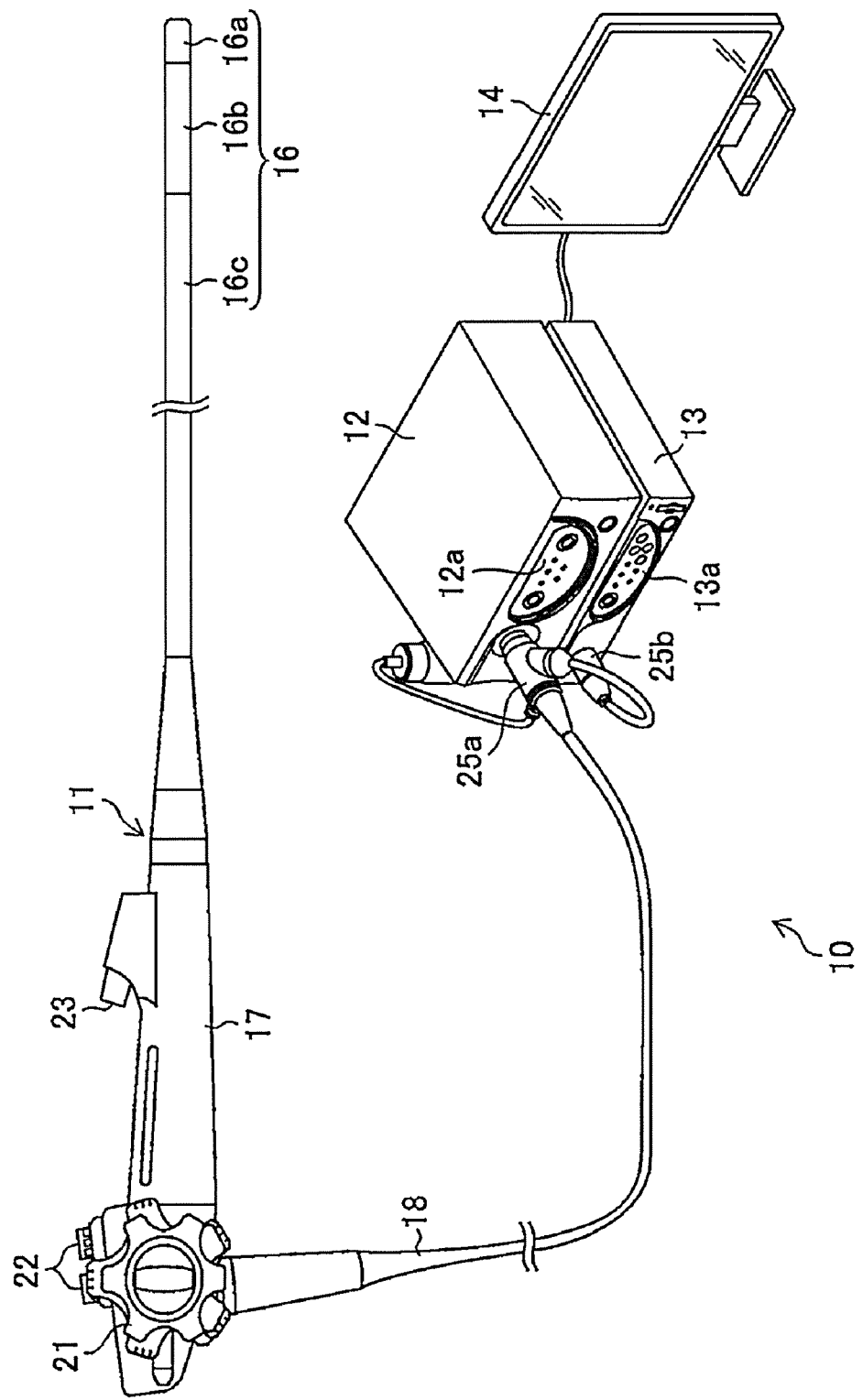
FIG. 1 is an external perspective view of an endoscope apparatus.

FIG. 1 is an external perspective view of an endoscope apparatus 10.

As illustrated in FIG. 1, the endoscope apparatus 10 includes, as its major units, an endoscope (here, a soft endoscope) 11 that captures images of an observation target in a subject, a light source device 12, a processor device 13, and a display 14, which is, for example, a liquid crystal monitor. In the following description, a case where the endoscope image processing apparatus according to the present invention is installed in the processor device 13 is described. Note that the endoscope image processing apparatus can be installed in a device other than the processor device 13 and, for example, can be installed in a computer.

The light source device 12 supplies to the endoscope 11 various types of illumination light including white light for capturing a normal image and light in a specific wavelength range for capturing a special-light image.

The processor device 13 is a device that can also function as one form of the endoscope apparatus 10 and has a function of generating image data of a normal image and/or a special-light image for display or recording on the basis of an image signal acquired by the endoscope 11.

The display 14 displays, for example, a normal image or a special-light image on the basis of image data for display input from the processor device 13.

The endoscope 11 includes an insertion part 16 that is flexible and inserted into the subject, a handheld operation part 17 that is coupled to the proximal end part of the insertion part 16, is a grip for holding the endoscope 11, and is used to operate the insertion part 16, and a universal cord 18 that connects the handheld operation part 17 to the light source device 12 and to the processor device 13.

Figure 2:
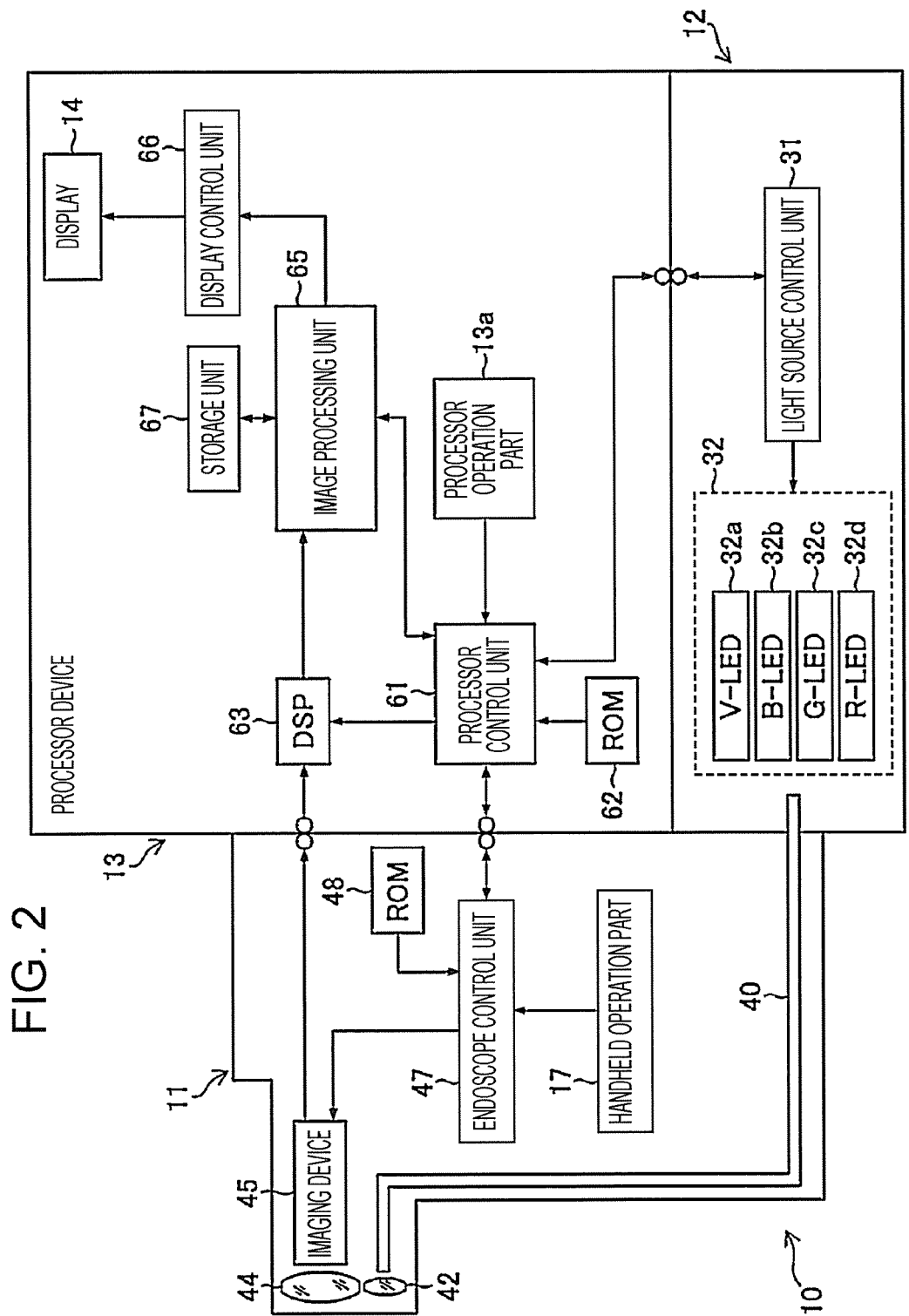
FIG. 2 is a block diagram illustrating an electric configuration of the endoscope apparatus.

In an insertion part tip part 16a, which is the tip part of the insertion part 16, for example, an illumination lens 42, an object lens 44, and an imaging device 45 are built (see FIG. 2). At the rear end of the insertion part tip part 16a, a bending part 16b that is bendable is coupled. At the rear end of the bending part 16b, a flexible pipe part 16c having flexibility is coupled. The insertion part tip part 16a and the bending part 16b constitute the scope head.

On the handheld operation part 17, for example, an angle knob 21, an operation button 22, and a forceps port 23 are provided. The angle knob 21 is rotated and operated to adjust the bending direction and the amount of bending of the bending part 16b. The operation button 22 is used to perform various operations including air supply, water supply, and suction. The forceps port 23 communicates with a forceps channel in the insertion part 16. Note that as the angle knob 21, an up-down angle knob for moving the bending part 16b upward and downward and a right-left angle knob for moving the bending part 16b rightward and leftward are provided.

In the universal cord 18, for example, an air-supply and/or water-supply channel, a signal cable, and a light guide 40 are incorporated. At the tip part of the universal cord 18, a connector part 25a that is connected to the light source device 12 and a connector part 25b that is connected to the processor device 13 are provided. Accordingly, illumination light is supplied to the endoscope 11 from the light source device 12 via the connector part 25a, and an image signal acquired by the endoscope 11 is input to the processor device 13 via the connector part 25b.

Note that on the light source device 12, a light source operation part 12a including, for example, a power button, a turn-on button for turning on the light source, and a brightness adjusting button is provided. On the processor device 13, a processor operation part 13a including a power button and a input unit that accepts input from a pointing device, such as a mouse, not illustrated is provided. Note that the processor operation part 13a functions as an operation input unit of the endoscope image processing apparatus.

FIG. 2 is a block diagram illustrating an electrical configuration of the endoscope apparatus 10.

As illustrated in FIG. 2, the endoscope 11 has, as its major units, the light guide 40, the illumination lens 42, the object lens 44, the imaging device 45, the handheld operation part 17, an endoscope control unit 47, and a ROM (read-only memory) 48.

As the light guide 40, for example, a large-diameter optical fiber or a fiber bundle is used. The entry end of the light guide 40 is inserted in the light source device 12 via the connector part 25a, and the exit end thereof passes through the insertion part 16 so as to face the illumination lens 42 provided in the insertion part tip part 16a. Illumination light supplied from the light source device 12 to the light guide 40 passes through the illumination lens 42 to irradiate an observation target. The illumination light is reflected and/or scattered at the observation target and enters the object lens 44.

The object lens 44 forms an image of the entering reflected light or scattered light resulting from the illumination light (that is, an optical image of the observation target) on the imaging surface of the imaging device 45.

The imaging device 45 is an imaging device of the CMOS (complementary metal-oxide semiconductor) type or the CCD (charge-coupled device) type and is positioned and fixed relative to the object lens 44 at a position on the further side than the object lens 44. On the imaging surface of the imaging device 45, a plurality of pixels formed of a plurality of photoelectric conversion elements (photodiodes) that photoelectrically convert the optical image are arranged in two dimensions. On the entry surface side of the plurality of pixels of the imaging device 45 in this example, a color filter of red (R), green (G), or blue (B) is arranged for each pixel to thereby form R pixels, G pixels, and B pixels. Note that the filter arrangement of the R, G, and B filters is typically based on the Bayer pattern but is not limited to this.

The imaging device 45 converts the optical image formed by the object lens 44 to an electric image signal and outputs the image signal to the processor device 13.

Note that in a case where the imaging device 45 is of the CMOS type, an A/D (analog/digital) converter is built therein, and a digital image signal is directly output from the imaging device 45 to the processor device 13. In a case where the imaging device 45 is of the CCD type, the image signal output from the imaging device 45 is converted to a digital image signal by, for example, an A/D converter not illustrated, and thereafter, the digital image signal is output to the processor device 13.

The handheld operation part 17 has a still-image capture button and an image capture mode setting unit for setting a normal-image capture mode and a special-light image capture mode.

The endoscope control unit 47 reads from, for example, the ROM 48 various programs and data and successively executes the programs in response to an operation on the handheld operation part 17 to mainly control driving of the imaging device 45. For example, in the normal-image capture mode, the endoscope control unit 47 controls the imaging device 45 so as to read signals from the R pixels, G pixels, and B pixels of the imaging device 45. In the special-light image capture mode and in a case where violet light is emitted from a V-LED 32a as illumination light or in a case where blue light is emitted from a B-LED 32b as illumination light in order to acquire a special-light image, the endoscope control unit 47 controls the imaging device 45 so as to only read signals from the B pixels of the imaging device 45 having spectral sensitivity in the wavelength ranges of the violet light and the blue light.

The endoscope control unit 47 communicates with a processor control unit 61 of the processor device 13 to transmit to the processor device 13, for example, input operation information input at the handheld operation part 17 and identification information for identifying the type of the endoscope 11 stored in the ROM 48.

The light source device 12 has a light source control unit 31 and a light source unit 32. The light source control unit 31 controls the light source unit 32 and communicates with the processor control unit 61 of the processor device 13 to exchange various types of information.

The light source unit 32 has, for example, a plurality of semiconductor light sources. In this embodiment, the light source unit 32 has LEDs of four colors, namely, the V-LED (Violet Light Emitting Diode) 32*a*, the B-LED (Blue Light Emitting Diode) 32*b*, a G-LED (Green Light Emitting Diode) 32*c*, and an R-LED (Red Light Emitting Diode) 32*d*. The V-LED 32*a* is a violet light source that emits violet light in a wavelength range from 380 to 420 nm and has a center wavelength of 405 nm. The B-LED 32*b* is a blue semiconductor light source that emits blue light in a wavelength range from 420 to 500 nm and has a center wavelength of 460 nm. The G-LED 32*c* is a green semiconductor light source that emits green light in a wavelength range from 480 to 600 nm. The R-LED 32*d* is a red semiconductor light source that emits red light in a wavelength range from 600 to 650 nm and has a center wavelength of 620 to 630 nm. Note that the center wavelengths of the V-LED 32*a* and the B-LED 32*b* have a width of about ±5 nm to ±10 nm.

The light source control unit 31 can separately control, for example, tuning on and off of the LEDs 32*a* to 32*d* and the amounts of light emission thereof during turning on, by inputting control signals independent of each other to the respective LEDs. In the normal-image capture mode, the light source control unit 31 turns on all of the V-LED 32*a*, the B-LED 32*b*, the G-LED 32*c*, and the R-LED 32*d*. Accordingly, in the normal-image capture mode, white light including violet light, blue light, green light, and red light is used as the illumination light.

On the other hand, in the special-light observation mode, the light source control unit 31 turns on one light source among the V-LED 32*a*, the B-LED 32*b*, the G-LED 32*c*, and the R-LED 32*d* or a plurality of light sources obtained by combining some of the LEDs as appropriate. In a case where the light source control unit 31 turns on a plurality of light sources, the light source control unit 31 controls the amounts of light emission of the respective light sources (light amount ratio) to thereby enable capturing of images of a plurality of layers at different depths in the subject.

Light rays in the respective colors emitted from the LEDs 32*a* to 32*d* pass through an optical path coupling part formed of, for example, a mirror or a lens and a diaphragm mechanism (not illustrated) and enter the light guide 40 inserted in the endoscope 11.

Note that as the illumination light of the light source device 12, light in various wavelength ranges suitable for the observation, that is, for example, white light (light in the wavelength range of white or light in a plurality of wavelength ranges), light in one or more specific wavelength ranges (special light), or a combination thereof, is selected. The specific wavelength range of the special light is a range narrower than the wavelength range of white.

A first example of the specific wavelength range is, for example, the blue range or the green range in the visible range. The wavelength range of the first example includes a wavelength range of 390 nm or more and 450 nm or less or 530 nm or more and 550 nm or less, and light of the first example has its peak wavelength in a wavelength range of 390 nm or more and 450 nm or less or 530 nm or more and 550 nm or less.

A second example of the specific wavelength range is, for example, the red range in the visible range. The wavelength range of the second example includes a wavelength range of 585 nm or more and 615 nm or less or 610 nm or more and 730 nm or less, and light of the second example has its peak wavelength in a wavelength range of 585 nm or more and 615 nm or less or 610 nm or more and 730 nm or less.

A third example of the specific wavelength range includes a wavelength range in which the light absorption coefficient differs between oxyhemoglobin and reduced hemoglobin, and light of the third example has its peak wavelength in a wavelength range in which the light absorption coefficient differs between oxyhemoglobin and reduced hemoglobin. The wavelength range of the third example includes a wavelength range of 400±10 nm, 440±10 nm, 470±10 nm, or 600 nm or more and 750 nm or less, and light of the third example has its peak wavelength in a wavelength range of 400±10 nm, 440±10 nm, 470±10 nm, or 600 nm or more and 750 nm or less described above.

A fourth example of the specific wavelength range is the wavelength range (from 390 nm to 470 nm) of excitation light that is used in observation (fluorescence observation) of fluorescence emitted from a fluorescent substance in the living body and that excites the fluorescent substance.

A fifth example of the specific wavelength range is the wavelength range of infrared light. The wavelength range of the fifth example includes a wavelength range of 790 nm or more and 820 nm or less or 905 nm or more and 970 nm or less, and light of the fifth example has its peak wavelength in a wavelength range of 790 nm or more and 820 nm or less or 905 nm or more and 970 nm or less.

The processor device 13 has, for example, the processor operation part 13*a*, the processor control unit 61, a ROM 62, a digital signal processing circuit (DSP: Digital Signal Processor) 63, an image processing unit 65, a display control unit 66, and a storage unit 67.

The processor operation part 13*a* includes, for example, the power button and the input unit that accepts input of, for example, a coordinate position that is specified on the display 14 with the mouse and a click (instruction for execution).

The processor control unit 61 reads from the ROM 62 necessary programs and data and successively performs processes in accordance with input operation information input at the processor operation part 13*a* and input operation information input at the handheld operation part 17 and received via the endoscope control unit 47 to thereby control the units of the processor device 13 and control the light source device 12. Note that the processor control unit 61 may accept necessary instructions input from another external device, such as a keyboard, connected via an interface not illustrated.

The DSP 63 that acquires pieces of image data of frames of a moving image output from the endoscope 11 (imaging device 45) performs in accordance with control by the processor control unit 61, various types of signal processing including, for example, defect correction, offsetting, white balance correction, gamma correction, and demosaicing for image data of one frame of the moving image input from the endoscope 11 to generate image data of the one frame.

The image processing unit 65 receives image data from the DSP 63 and preforms image processing including, for example, color conversion, color enhancement, and structural enhancement for the received image data as necessary to generate image data representing an endoscopic image in which the observation target is present. The color conversion is a process for converting colors by performing, for example, a 3×3 matrix process, gradation transformation, and a three-dimensional look-up table process for the image data. The color enhancement is a process for enhancing colors for the image data subjected to the color conversion such that, for example, the tint of blood vessels and that of a mucous membrane are made different. The structural enhancement is a process for enhancing a specific tissue or structure included in the observation target, which is, for example, a blood vessel or a pit pattern, and is performed for the image data subjected to the color enhancement.

In response to an image capture instruction for a still image or a moving image, pieces of image data of the respective frames of the moving image processed by the image processing unit 65 are recorded to the storage unit 67 as the still image or the moving image for which the image capture instruction has been given.

The display control unit 66 generates from received image data, display data for displaying a normal image or a special-light image on the display 14 and outputs the generated display data to the display 14 to display a display image on the display 14.

Figure 3:
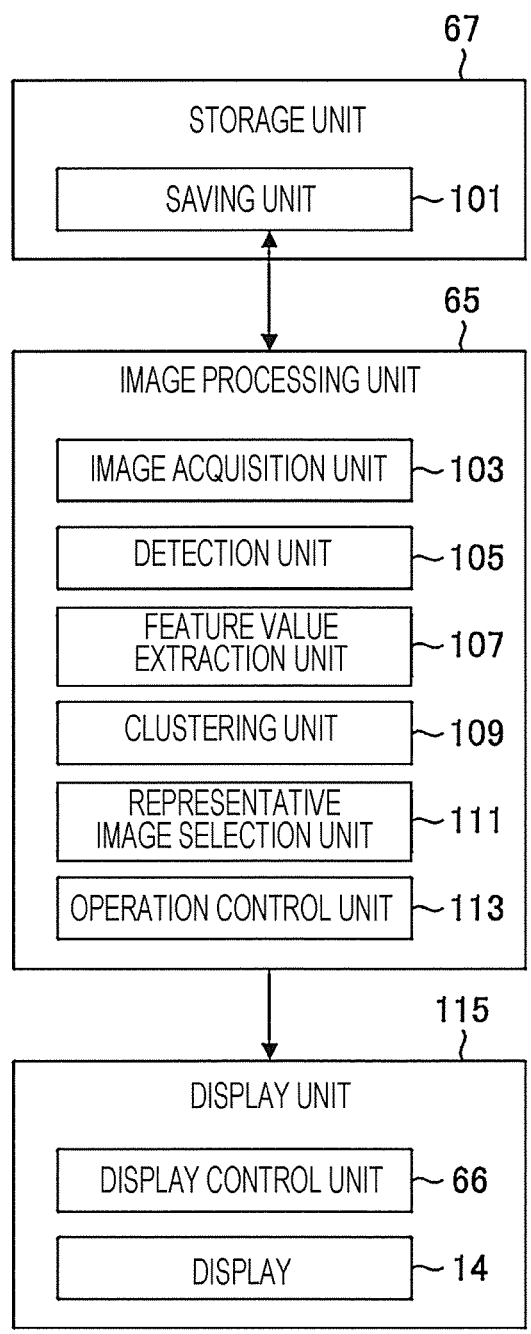
FIG. 3 is a block diagram illustrating the functions of the endoscope apparatus.

FIG. 3 is a block diagram illustrating the major functions of the endoscope apparatus 10 according to the present invention.

A saving unit 101 is provided in the storage unit 67, and an image acquisition unit 103, a detection unit 105, a feature value extraction unit 107, a clustering unit 109, a representative image selection unit 111, and an operation control unit 113 are provided in the image processing unit 65. A display unit 115 is formed of the display control unit 66 and the display 14.

The image acquisition unit 103 acquires endoscopic images. The image acquisition unit 103 in this example acquires endoscopic images from the endoscope 11 in real time. In a case where the endoscope image processing apparatus is installed in a computer that is not directly connected to the endoscope 11, the image acquisition unit 103 acquires endoscopic images already captured and saved during an endoscopic examination. When the image acquisition unit 103 acquires an endoscopic image, supplementary information (second supplementary information) including the time at which the endoscopic image was captured, the image capture conditions (for example, the scale of enlargement) of the endoscopic image, and image capture light source information may be acquired in association with the endoscopic image. The endoscopic image and supplementary information acquired by the image acquisition unit 103 are saved in the saving unit 101.

The detection unit 105 detects a lesion image representing a lesion in an endoscopic image acquired by the image acquisition unit 103. Here, a lesion represented by a lesion image is a concept that includes the lesion itself or a lesion region including the lesion itself and its surrounding part. Note that the detection unit 105 detects a lesion image using a publicly known technique, and therefore, a description thereof is omitted here.

The feature value extraction unit 107 extracts an image feature value of a lesion image detected by the detection unit 105. The feature value extraction unit 107 can extract an image feature value of a lesion image by using various methods. For example, the feature value extraction unit 107 extracts feature vectors corresponding to respective lesion images. In this case, the clustering unit 109 assumes that lesion images for which the degree of correlation between their feature vectors is equal to or higher than a threshold value are to belong to the same group and generates a group. Examples of the feature vector include a histogram of the image, a BoVW (Bag of Visual Words) vector, and a feature vector based on a neural network.

The clustering unit 109 compares endoscopic images saved in the saving unit 101 and generates a group of endoscopic images having the same lesion. The clustering unit 109 groups endoscopic images on the basis of the degree of correlation between the lesion images to generate, for each lesion, a group formed of endoscopic images. The clustering unit 109 can calculate the degree of correlation by using various methods. The clustering unit 109 calculates the degree of correlation by comparing image feature values extracted by the feature value extraction unit 107.

The clustering unit 109 may calculate the degree of correlation by using second supplementary information saved in association with an endoscopic image. The second supplementary information is information that is a supplement to an acquired endoscopic image and includes the time at which the endoscopic image was captured, the image capture conditions (for example, the scale of enlargement) of the endoscopic image, and image capture light source information. The clustering unit 109 may calculate the degree of correlation by using, for example, the examination time, the frame number, the position of the endoscope 11, and the type of lesion. Further, the clustering unit 109 may calculate the degree of correlation for some of the endoscopic images saved in the saving unit 101 to generate a group. From the viewpoint of generating a group for each lesion, the clustering unit 109 may calculate the degree of correlation by comparing, for example, endoscopic images for which their examination times are within a predetermined range to generate a group.

The clustering unit 109 may calculate the degree of correlation by using a plurality of pieces of information. Even in a case where the degree of correlation between the feature vectors of endoscopic images is equal to or lower than a threshold value, when the times at which the endoscopic images were captured are closer than a threshold value, the clustering unit 109 may assume that the endoscopic images are to belong to the same group. Further, a feature vector extractor suitable for identifying each image capture light source may be prepared, and the clustering unit 109 may calculate the degree of correlation between endoscopic images captured by using the same image capture light source.

The saving unit 101 saves images (including information that is a supplement thereto) acquired by the image acquisition unit 103 and/or endoscopic images grouped by the clustering unit 109. Further, the saving unit 101 also saves information regarding lesion images detected by the detection unit 105.

FIGS. 4A and 4B and FIGS. 5A and 5B are diagrams for describing example saving configurations of the saving unit 101.

Figure 4:
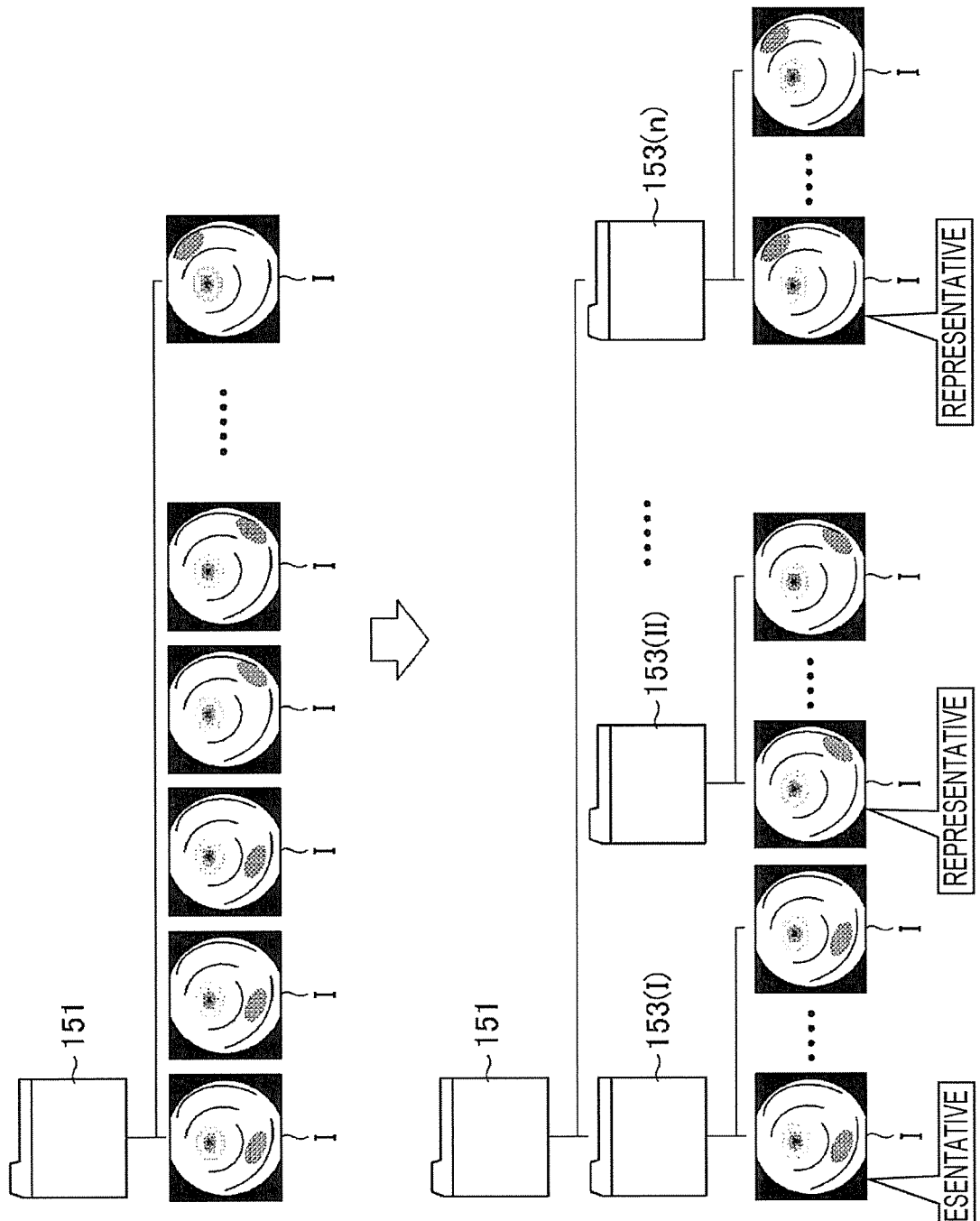
FIGS. 4A and 4B are diagrams for describing example saving configurations.

FIGS. 4A and 4B are diagrams illustrating an example where saving is performed on a per group basis by using folders. FIG. 4A illustrates a saving configuration for endoscopic images before grouping acquired by the image acquisition unit 103, and FIG. 4B illustrates a saving configuration for the endoscopic images after grouping by the clustering unit 109.

In the case illustrated in FIG. 4A, acquired endoscopic images are saved in the same folder 151. That is, endoscopic images I saved in the folder 151 are not grouped and arranged in the order in which, for example, the images have been captured. The plurality of endoscopic images I saved in the folder 151 are grouped by the clustering unit 109.

In FIG. 4B, a group folder 153(I), a group folder 153(II), and a group folder 153(n) are generated for respective groups generated by the clustering unit 109. Note that n indicates the number of groups generated by the clustering unit 109. The endoscopic images I in each group are saved in a corresponding one of the group folders 153. Further, an endoscopic image I that is saved first (captured earliest) among the endoscopic images I in each group is assumed to be a representative image. Selection of a representative image will be described below. Further, the group folders 153 are generated under the folder 151.

Figure 5:
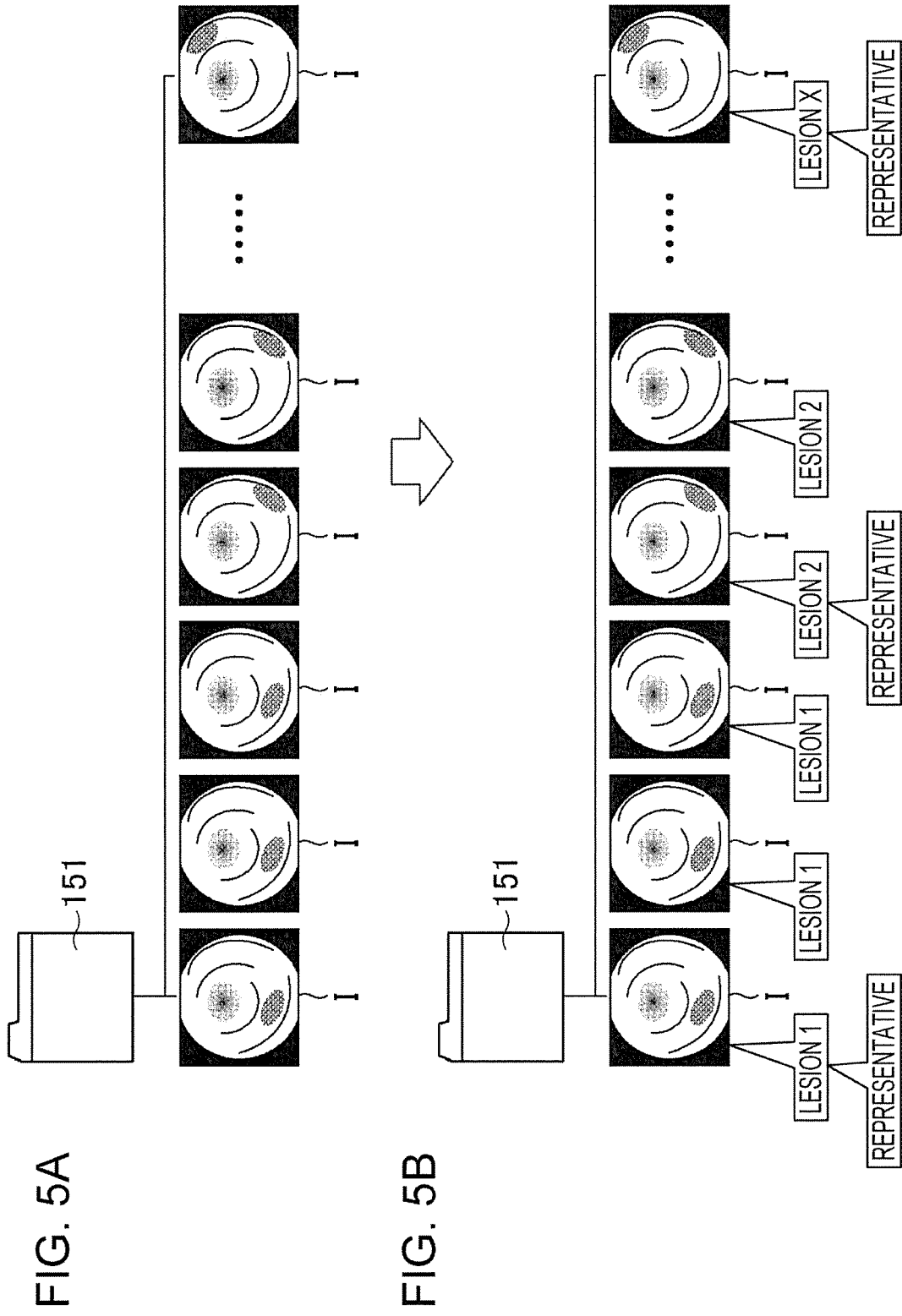
FIGS. 5A and 5B are diagrams for describing example saving configurations.

FIGS. 5A and 5B are diagrams illustrating an example where the grouped endoscopic images I are saved while identification ID information is added to each endoscopic image. FIG. 5A illustrates a saving configuration for endoscopic images before grouping acquired by the image acquisition unit 103, and FIG. 5B illustrates a saving configuration for the endoscopic images after grouping by the clustering unit 109.

In FIG. 5A, acquired endoscopic images are saved in the same folder 151. In FIG. 5B, each endoscopic image I is given a group identification ID. Specifically, each endoscopic image I is given a group identification ID indicating lesion 1, a group identification ID indicating lesion 2, or a group identification ID indicating lesion X. A representative image is given identification indicating that the image is a representative image.

Further, the saving unit 101 saves a representative image and endoscopic images that form the group to which the representative image belongs in association with each other as illustrated in FIGS. 4A and 4B and FIGS. 5A and 5B.

The representative image selection unit 111 selects a representative image from among the endoscopic images in a group. The representative image selection unit 111 selects at least one representative image in each group from among the endoscopic images saved in the saving unit 101 on a per lesion basis. Selection of a representative image by the representative image selection unit 111 is made in accordance with a preset selection rule. As a selection criterion for the representative image selection unit 111, among the endoscopic images in a group, for example, an endoscopic image captured earliest, an endoscopic image captured with white light, an endoscopic image that is blurred to the smallest degree, an endoscopic image in which a lesion is present closest to the center, or an endoscopic image captured without enlargement is selected as a representative image. Here, an endoscopic image captured without enlargement is an endoscopic image that is captured without enlargement so as to grasp a lesion and its surroundings.

The representative image selection unit 111 may select a single representative image or a plurality of representative images from each group. For example, for a single lesion (group), the representative image selection unit 111 may select one representative image for each image capture light source. For example, the representative image selection unit 111 may acquire a WL (white light) representative image, an LCI (linked-color imaging) representative image, and a BLI (blue laser imaging) representative image for the respective light sources. Note that the LCI light source is a light source that emits narrow-band short-wavelength light and white light simultaneously to enhance slight closeness in colors.

The operation control unit 113 performs, for a representative image, an operation accepted by the operation input unit (processor operation part 13a). In this case, the operation control unit 113 may perform the accepted operation only for the representative image or may perform the accepted operation for the representative image and all endoscopic image in the group to which the representative image belongs.

The display unit 115 displays a list of representative images saved in the saving unit 101. The display unit 115 displays endoscopic images saved in the saving unit 101 on the display 14 in accordance with control by the display control unit 66. It is preferable to set the display form of the display unit 115 so as to be suitable for the user, and the user can set the display form of the display unit 115 as appropriate. For example, the display unit 115 can change the number of columns of list display of representative images (see reference numeral 170 in FIG. 6).

Figure 6:
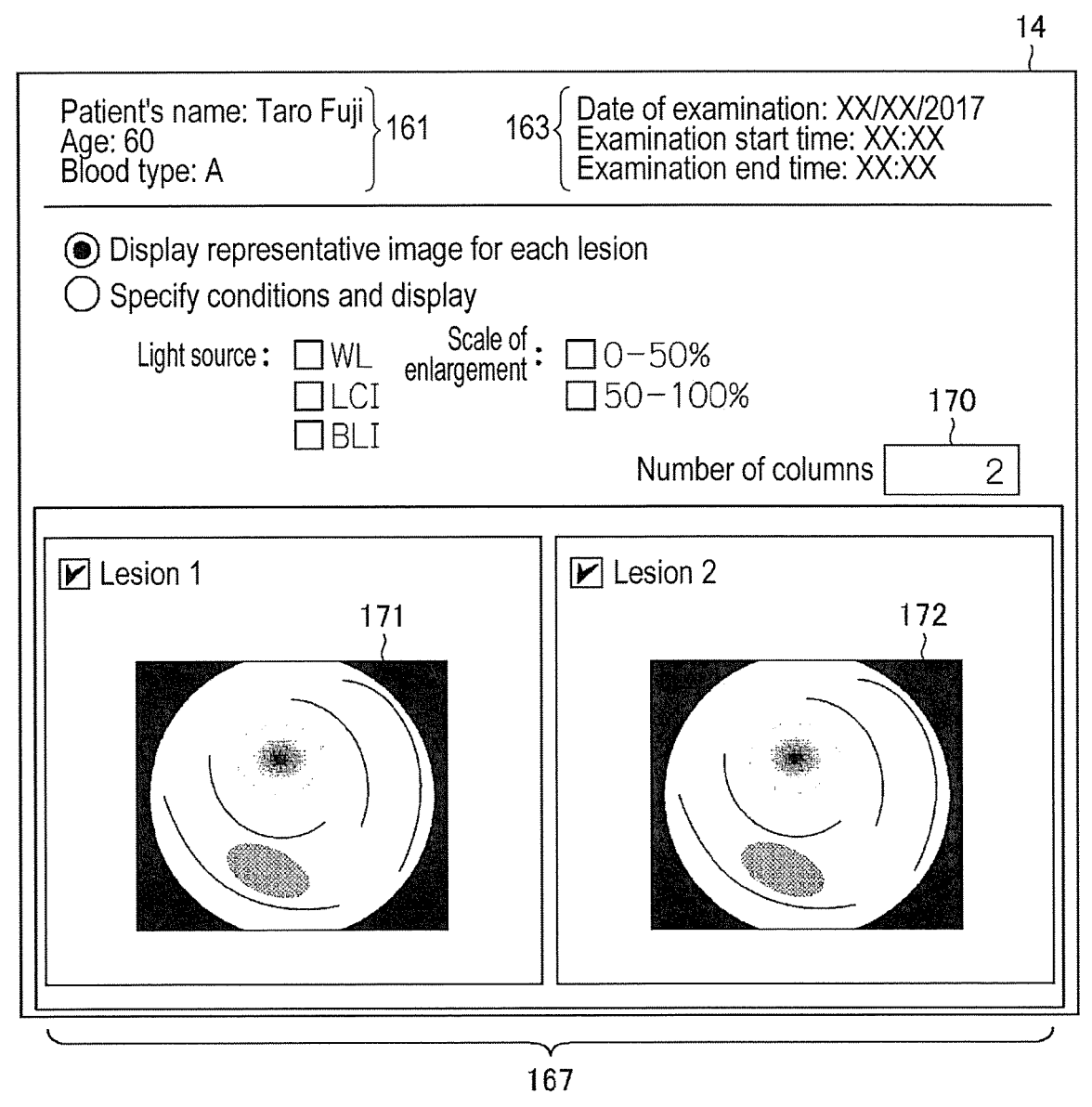

FIG. 6 is a diagram for describing example list display of representative images by the display unit 115.

The display unit 115 displays list display 167 of representative image. The list display 167 is formed of a representative image 171 of the group of lesion 1 and a representative image 172 of the group of lesion 2. In addition to the list display 167, information 161 about a patient who has undergone the endoscopic examination and information 163 about the performed endoscopic examination are displayed. The number of columns to be displayed can be changed by the user as appropriate. In the illustrated case, "2" is selected as the number of columns, and a list of the representative images are displayed in two columns (see reference numeral 170).

Selection of Endoscopic Images

Now, selection of endoscopic images that form a group is described. The user selects an image displayed on the display unit 115 by placing a marker, such as an arrow, displayed by the display unit 115 on the image and clicking the mouse (pointing device). In this case, when selection is made by the user, only the displayed representative image can be selected or all images in the group to which the representative image belongs can be collectively selected. The user selects a representative image or selects a representative image and endoscopic images in the group to which the representative image belongs, and adds information including the results of diagnosis.

Figure 7:
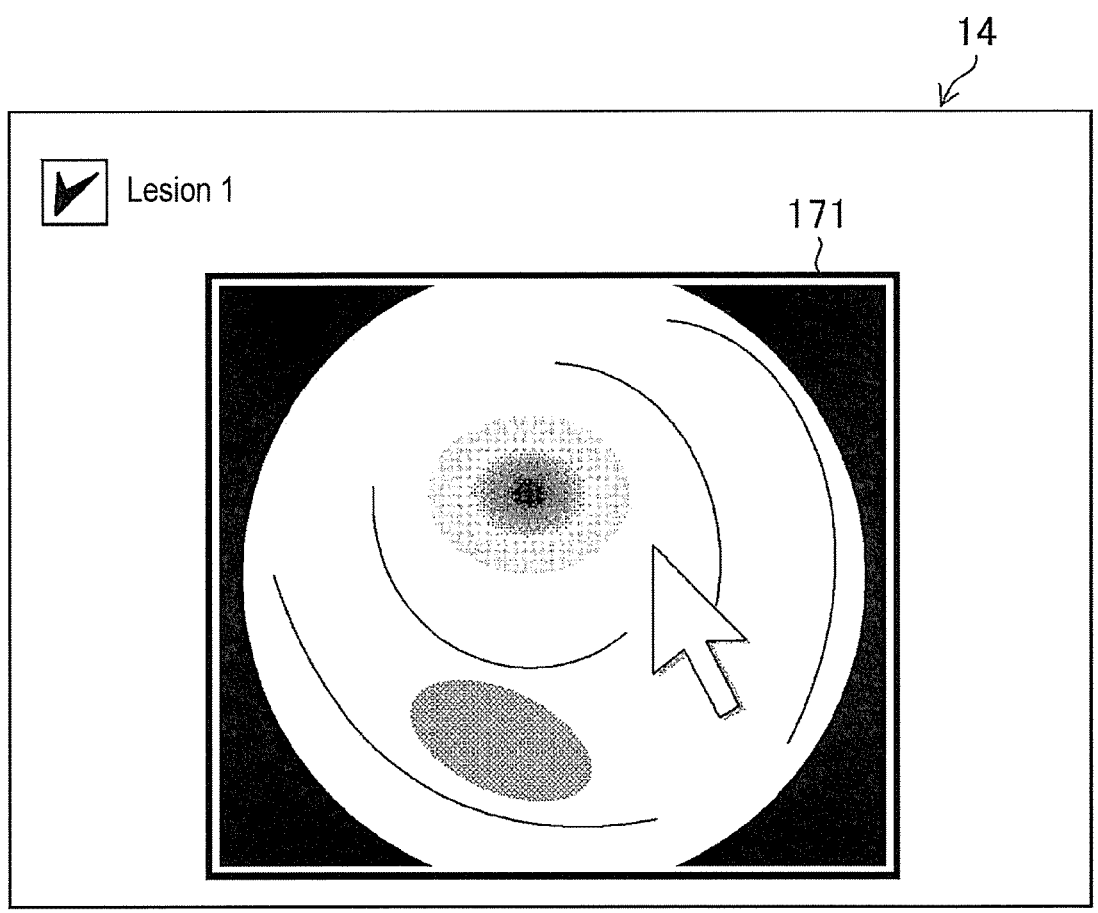
FIG. 7 is a diagram illustrating example selection of a representative image.
Figure 8:
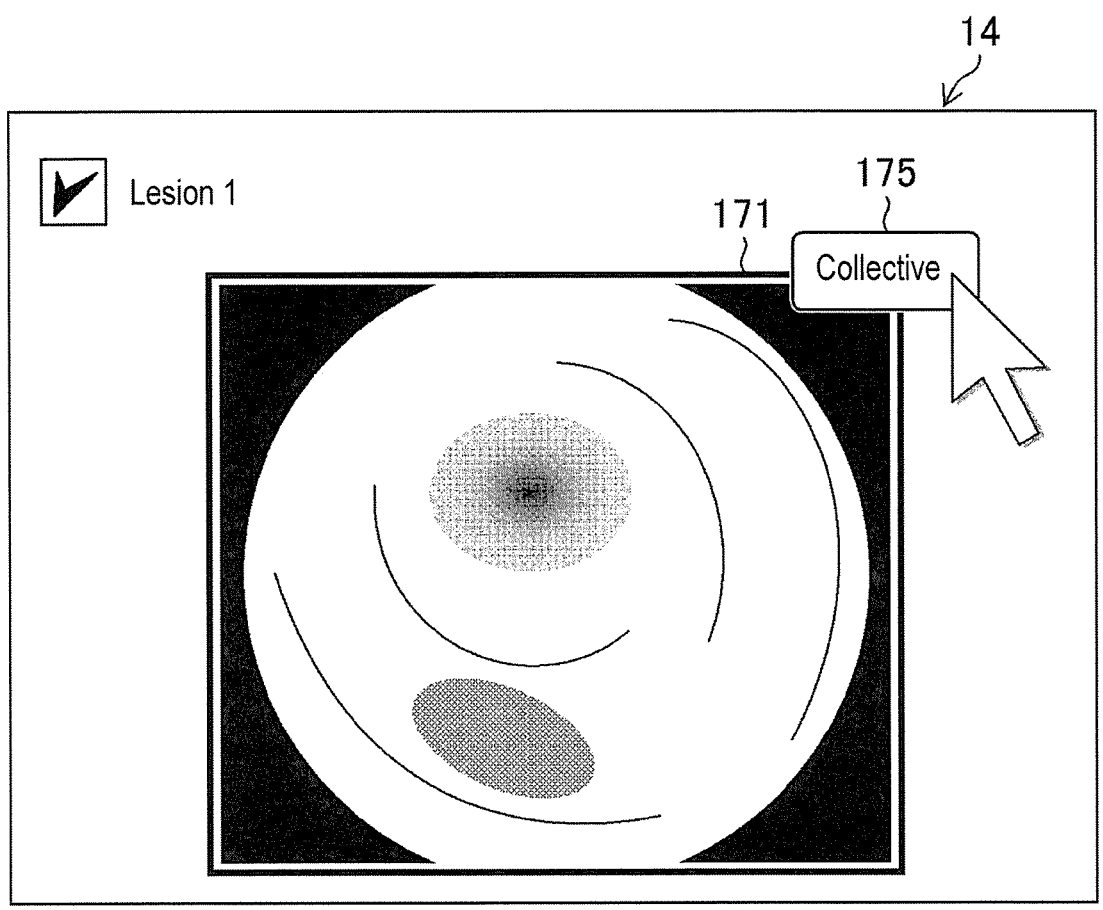
FIG. 8 is a diagram illustrating example selection of a representative image.

FIG. 7 and FIG. 8 are diagrams illustrating example selection of a representative image displayed by the display unit 115. In the example illustrated in FIG. 7, the representative image 171 is selected by a click, and only the representative image 171 is selected. In the example illustrated in FIG. 8, the user clicks on a collective selection button 175, and the representative image 171 and endoscopic images that form the group to which the representative image 171 belongs are selected.

Note that selection of endoscopic images is not limited to the forms described with reference to FIG. 7 and FIG. 8. For example, the user may click on a representative image with the mouse to select only the representative image, or the user may double-click on a representative image with the mouse to collectively select endoscopic images that form the group. In a case where a representative image is selected by pressing a certain key and clicking the mouse, all endoscopic image in the group to which the representative image belongs may be selected.

Addition of Information to Endoscopic Images

Now, addition of information to a representative image and to endoscopic images in the group to which the representative image belongs is described.

Figure 9:
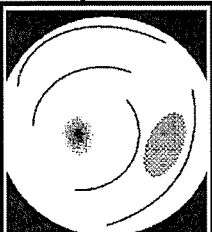
FIG. 9A and FIG. 9B are diagrams illustrating a form of a transition from a normal list-display mode to an additional-information input mode.

FIGS. 9A and 9B are diagrams illustrating a form of a transition from a normal list-display mode to an additional-information input mode. FIG. 9A illustrates the display form in the normal list-display mode as in FIG. 6. Here, the normal list-display mode is a mode in which a list of representative images of respective groups are displayed. Note that a part already described with reference to FIG. 6 is assigned the same reference numeral, and a description thereof is omitted. FIG. 9B illustrates the display form of the display unit 115 in the additional-information input mode.

A transition from the normal list-display mode to the additional-information input mode occurs when a predetermined operation is input. When information is added in the additional-information input mode, the information is added to a selected image (a representative image or all endoscopic images in the group). For example, as illustrated in FIG. 9B, additional information (first supplementary information) 181 including the result of diagnosis of the lesion, the category of the lesion, the position of the lesion, and the size of the lesion is added to the representative image 171. In this example, the representative image 171 and endoscopic images in the group to which the representative image 171 belongs are selected, and therefore, the same information is added also to the endoscopic images in the group to which the representative image 171 belongs. Specifically, the user uses the operation input unit to input first supplementary information to be added to the representative image, and the operation control unit 113 adds the first supplementary information to all endoscopic images in the group to which the representative image belongs.

Figure 10:
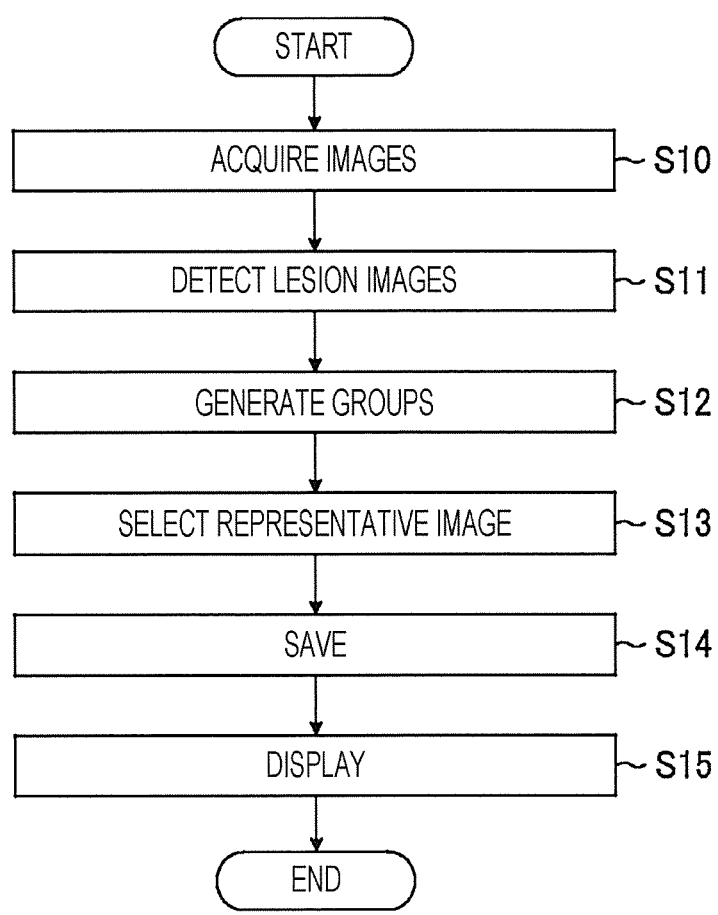
FIG. 10 is a flowchart illustrating process steps of the endoscope image processing apparatus.

Now, the endoscope image processing method using the endoscope image processing apparatus is described. FIG. 10 is a flowchart illustrating process steps of the endoscope image processing apparatus.

First, the image acquisition unit 103 acquires endoscopic images (step S10: image acquisition step). Thereafter, the detection unit 105 detects lesion images (step S11: detection step). The clustering unit 109 generates a group for each lesion (step S12: clustering step). Thereafter, the representative image selection unit 111 selects a representative image of each group (step S13: representative image selection step). Thereafter, the representative image of each group and endoscopic images that form the group are saved in the saving unit 101 (step S14: saving step), and the display unit 115 displays a list of the representative images saved in the saving unit 101 (step S15: display step).

In the above-described embodiment, the hardware configuration of the processing units that perform various types of processing is implemented as various processors as described below. The various processors include a CPU (central processing unit), which is a general-purpose processor executing software (program) to function as various processing units, a programmable logic device (PLD), such as an FPGA (field-programmable gate array), which is a processor having a circuit configuration that is changeable after manufacture, and a dedicated electric circuit, such as an ASIC (application-specific integrated circuit), which is a processor having a circuit configuration specifically designed to perform specific processing.

One processing unit may be configured as one of the various processors or two or more processors of the same type or different types (for example, a plurality of FPGAs or a combination of a CPU and an FPGA). Further, a plurality of processing units may be configured as one processor. As the first example of configuring a plurality of processing units as one processor, a form is possible where one or more CPUs and software are combined to configure one processor, and the processor functions as the plurality of processing units, a representative example of which is a computer, such as a client or a server. As the second example thereof, a form is possible where a processor is used in which the functions of the entire system including the plurality of processing units are implemented as one IC (integrated circuit) chip, a representative example of which is a system on chip (SoC). As described above, regarding the hardware configuration, the various processing units are configured by using one or more of the various processors described above.

Further, the hardware configuration of the various processors is more specifically an electric circuit (circuitry) in which circuit elements, such as semiconductor elements, are combined.

The above-described configurations and functions can be implemented as any hardware, software, or a combination thereof as appropriate. For example, the present invention is applicable to a program that causes a computer to perform the above-described processing steps (processing procedure), a computer-readable recording medium (non-transitory recording medium) to which such a program is recorded, or a computer in which such a program can be installed.

As described above, according to this aspect, a group formed for each lesion is generated, a representative image of each generated group is selected, each representative image and endoscopic images that form the group to which the representative image belongs are saved in association with each other, and a list of the representative images are displayed. Accordingly, the user's workload is reduced, and efficient operations are performed. Further, endoscopic images (non-representative images), other than the representative image, that form the group are essential information, and the non-representative images are managed together with the representative image to thereby provide efficient operations to the user.

Example Application 1

In this example, groups generated by the clustering unit 109 can be modified. After groups have been generated by the clustering unit 109, the user performs an operation for a representative image via the operation input unit to modify the group as desired.

The operation input unit in this example accepts, for a representative image, a change command for changing the group formation of the group. The operation control unit 113 carries out the accepted change command for all endoscopic images in the group to which the representative image belongs.

As an example change command for changing a group formation accepted by the operation input unit, the user selects at least two representative images of groups that the user wants to integrate and clicks on a button (not illustrated) having a function of integrating groups. Alternatively, the user selects at least one representative image by, for example, clicking the mouse, moves the representative image onto another representative image while holding down the mouse button, and releases the mouse button, that is, performs a drag-and-drop operation, to thereby input a change command. In the additional-information input mode, the identification ID of the group to which the representative image belongs may be changed to the identification ID of the integration destination.

Example Application 2

In this example, the display form of list display of representative images by the display unit 115 is changed.

Figure 11:
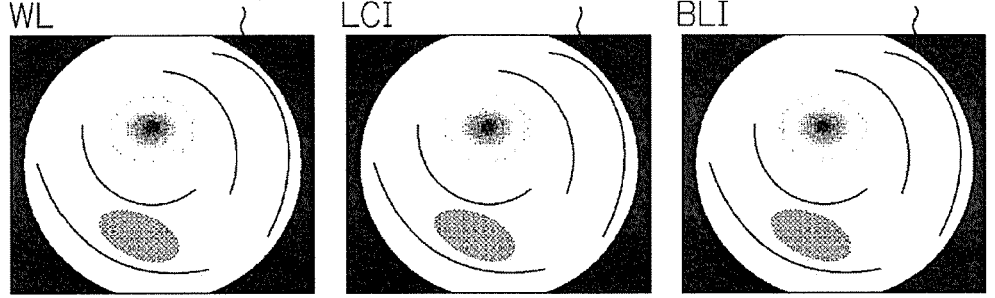
FIG. 11 is a diagram illustrating example display by a display unit.

FIG. 11 is a diagram illustrating example display by the display unit 115. Note that a part already described with reference to FIG. 6 is assigned the same reference numeral, and a description thereof is omitted.

In this example, a display form selection part 191 that accepts a selection command for selecting a display form of list display by the display unit 115 is provided. The display unit 115 displays a list of representative images on the basis of the result of selection in the display form selection part 191. The display form selection part 191 includes selection items, namely, "display representative image for each lesion" and "specify conditions and display". For "specify conditions and display", selection items of light source (WL, LCI, and BLI) and scale of enlargement are provided. The user selects these selection items as appropriate to select a display form of list display of representative images. In the case illustrated in FIG. 11, "display representative image for each lesion" and "specify conditions and display" are selected, and selection is made so as to display representative images captured by using the light sources WL, LCI, and BLI. Therefore, the display unit 115 displays a list of a representative image 193 captured by using the light source WL, a representative image 195 captured by using the light source LCI, and a representative image 197 captured by using the light source BLI in the group of lesion 1.

Example Application 3

In this example, a representative image is changed on the basis of user input.

Figure 12:
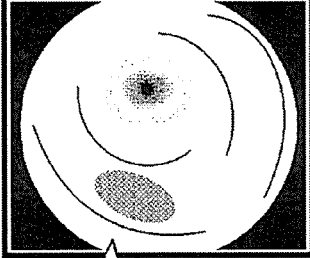
FIG. 12 is a diagram illustrating example display by the display unit.

FIG. 12 is a diagram illustrating example display by the display unit 115. Note that a part already described with reference to FIG. 6 is assigned the same reference numeral, and a description thereof is omitted.

In this example, when the representative image 171 is selected, an endoscopic image 201, an endoscopic image 203, an endoscopic image 205, an endoscopic image 207, and an endoscopic image 209 in the group of lesion 1 are displayed in a representative image change part 199. The user selects the endoscopic image 205 that the user wants to set as the representative image from among the endoscopic images (201, 203, 205, 207, and 209) displayed in the representative image change part 199 to thereby input a change command for changing the representative image. The representative image selection unit 111 changes the representative image to the different endoscopic image on the basis of the change command. Specifically, the representative image selection unit 111 changes the representative image of the group of lesion 1 to the endoscopic image 205 on the basis of the input change command.

Note that as the display form of the representative image change part 199, various forms other than the example described with reference to FIG. 12 can be employed. For example, the user rotates a mouse wheel on a representative image, an endoscopic image in the group is displayed in accordance with the amount of rotation, and the user changes the representative image. Alternatively, when a representative image is selected, a list of endoscopic images in the group are displayed in a separate window, and the user selects an image from among the endoscopic images to change the representative image.

Examples of the present invention have been described above; however, the present invention is not limited to the above-described embodiment, and various modifications can be made without departing from the spirit of the present invention as a matter of course.

REFERENCE SIGNS LIST 10 endoscope apparatus
11 endoscope
12 light source device
12a light source operation part
13 processor device
13a processor operation part
14 display
16 insertion part
16a insertion part tip part
16b bending part
16c flexible pipe part
17 handheld operation part
18 universal cord
21 angle knob
22 operation button
23 forceps port
25a connector part
25b connector part
31 light source control unit
32 light source unit
32a V-LED
32b B-LED
32c G-LED
32d R-LED
40 light guide
42 illumination lens
44 object lens
45 imaging device
47 endoscope control unit
48 ROM
61 processor control unit
62 ROM
65 image processing unit
66 display control unit
67 storage unit
101 saving unit
103 image acquisition unit
105 detection unit
107 feature value extraction unit
109 clustering unit
111 representative image selection unit
113 operation control unit
115 display unit

What is claimed is:

1. An endoscope image processing apparatus comprising:
a processor configured to:
acquire endoscopic images;
detect lesion images representing lesions in the endoscopic images;
group the endoscopic images on the basis of a degree of correlation between the lesion images and generates, for each lesion, a group formed of corresponding ones of the endoscopic images; and
select, for each group, a representative image from among the endoscopic images in the group;
a memory that saves, for each group, the representative image and the endoscopic images that form the group to which the representative image belongs, wherein the representative image and the endoscope images are saved in a same folder or the representative image and the endoscope images are given a same identification; and a display that displays a list of the representative images saved in the memory.

2. The endoscope image processing apparatus according to claim 1, wherein the processor is further configured to:
accept an operation for a representative image among the representative images displayed on the display; and
uniformly perform the operation for all the endoscopic images in the group to which the representative image belongs.

3. The endoscope image processing apparatus according to claim 2, wherein
processor accepts input of first supplementary information to be added to the representative image, and
the processor adds the first supplementary information to all the endoscopic images in the group to which the representative image belongs.

4. The endoscope image processing apparatus according to claim 2, wherein
the processor accepts a change command for changing a group formation of the group, and
the processor carries out the change command for all the endoscopic images in the group to which the representative image belongs.

5. The endoscope image processing apparatus according to claim 3, wherein
the processor accepts a change command for changing a group formation of the group, and
the processor carries out the change command for all the endoscopic images in the group to which the representative image belongs.

6. The endoscope image processing apparatus according to claim 1, wherein the processor is further configured to:
extract image feature values of the lesion images, wherein
the processor calculates the degree of correlation on the basis the image feature values and generates the group on the basis of the degree of correlation.

7. The endoscope image processing apparatus according to claim 2, wherein the processor is further configured to:
extract image feature values of the lesion images, wherein
the processor calculates the degree of correlation on the basis the image feature values and generates the group on the basis of the degree of correlation.

8. The endoscope image processing apparatus according to claim 3, wherein the processor is further configured to:
extract image feature values of the lesion images, wherein
the processor calculates the degree of correlation on the basis the image feature values and generates the group on the basis of the degree of correlation.

9. The endoscope image processing apparatus according to claim 4, wherein the processor is further configured to:
extract image feature values of the lesion images, wherein
the processor calculates the degree of correlation on the basis the image feature values and generates the group on the basis of the degree of correlation.

10. The endoscope image processing apparatus according to claim 1, wherein
the processor acquires the endoscopic images having second supplementary information that is information about capturing of the endoscopic images, and
the processor calculates the degree of correlation by using the second supplementary information.

11. The endoscope image processing apparatus according to claim 2, wherein
the processor acquires the endoscopic images having second supplementary information that is information about capturing of the endoscopic images, and
the processor calculates the degree of correlation by using the second supplementary information.

12. The endoscope image processing apparatus according to claim 3, wherein
the processor acquires the endoscopic images having second supplementary information that is information about capturing of the endoscopic images, and
the processor calculates the degree of correlation by using the second supplementary information.

13. The endoscope image processing apparatus according to claim 4, wherein
the processor acquires the endoscopic images having second supplementary information that is information about capturing of the endoscopic images, and
the processor calculates the degree of correlation by using the second supplementary information.

14. The endoscope image processing apparatus according to claim 1, wherein the processor selects, as the representative image, an endoscopic image captured earliest, an endoscopic image captured with white light, an endoscopic image that is blurred to a smallest degree, an endoscopic image in which the lesion is present closest to a center, or an endoscopic image captured without enlargement from among the endoscopic images in the group.

15. The endoscope image processing apparatus according to claim 1, wherein the processor is further configured to:
accept a change command for changing the representative image, wherein
the processor changes the representative image to a different endoscopic image among the endoscopic images on the basis of the change command.

16. The endoscope image processing apparatus according to claim 1, wherein the processor is further configured to:
accept a selection command for selecting a display form of list display by the display, wherein
the display performs the list display on the basis of a result of selection.

17. The endoscope image processing apparatus according to claim 1, wherein the processor acquires the endoscopic images from an endoscope in real time.

18. The endoscope image processing apparatus according to claim 1, wherein the processor acquires the endoscopic images already captured and saved during an endoscopic examination.

19. An endoscope image processing method comprising:
acquiring endoscopic images;
detecting lesion images representing lesions in the endoscopic images;
grouping the endoscopic images on the basis of a degree of correlation between the lesion images and generating, for each lesion, a group formed of corresponding ones of the endoscopic images;
selecting, for each group, a representative image from among the endoscopic images in the group;
saving, for each group, the representative image and the endoscopic images that form the group to which the representative image belongs, wherein the representative image and the endoscope images are saved in a same folder or the representative image and the endoscope images are given a same identification; and
displaying a list of the representative images.

20. A non-transitory computer readable recording medium storing a program causing a computer to perform an endoscope image processing method comprising:
- acquiring endoscopic images;
- detecting lesion images representing lesions in the endoscopic images;
- grouping the endoscopic images on the basis of a degree of correlation between the lesion images and generating, for each lesion, a group formed of corresponding ones of the endoscopic images;
- selecting, for each group, a representative image from among the endoscopic images in the group;
- saving, for each group, the representative image and the endoscopic images that form the group to which the representative image belongs, wherein the representative image and the endoscope images are saved in a same folder or the representative image and the endoscope images are given a same identification; and
- displaying a list of the representative images.

* * * * *